United States Patent
Ye et al.

(10) Patent No.: US 8,486,371 B2
(45) Date of Patent: Jul. 16, 2013

(54) QUANTITATIVE TWO-PHOTON FLOW CYTOMETRY

(75) Inventors: Jing Yong Ye, Ann Arbor, MI (US); Theodore B. Norris, Dexter, MI (US); Cheng Frank Zhong, Sunnyvale, MI (US); James R. Baker, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 1361 days.

(21) Appl. No.: 11/662,835

(22) PCT Filed: Sep. 16, 2005

(86) PCT No.: PCT/US2005/033189
§ 371 (c)(1), (2), (4) Date: Apr. 4, 2008

(87) PCT Pub. No.: WO2006/034046
PCT Pub. Date: Mar. 30, 2006

(65) Prior Publication Data
US 2008/0292555 A1    Nov. 27, 2008

Related U.S. Application Data

(60) Provisional application No. 60/611,261, filed on Sep. 17, 2004.

(51) Int. Cl.
*A61K 49/00*    (2006.01)

(52) U.S. Cl.
USPC ........... 424/9.1; 424/1.11; 424/1.65; 424/9.6; 424/1.29

(58) Field of Classification Search
USPC .............. 424/1.29, 1.33, 1.37, 1.65, 9.1, 9.3, 424/9.4, 9.5, 9.6, 400, 450, 451, 463, 489, 424/490, 1.11
See application file for complete search history.

(56) References Cited

U.S. PATENT DOCUMENTS

| | | | |
|---|---|---|---|
| 5,909,278 A * | 6/1999 | Deka et al. | 356/318 |
| 6,761,877 B2 | 7/2004 | Barbera-Guillem | |
| 7,170,598 B2 * | 1/2007 | Walla et al. | 356/318 |
| 7,318,336 B2 * | 1/2008 | Roth et al. | 73/1.02 |

* cited by examiner

*Primary Examiner* — D L Jones
(74) *Attorney, Agent, or Firm* — Harness, Dickey & Pierce, P.L.C.

(57) ABSTRACT

A method and apparatus of multi-dye analysis of particles using flow cytometer. The method includes dying particles to be detected using two or more dyes; urging the particles through a capillary in a non-uniform flow; exciting a first of the particles within the capillary using a multiphoton excitation laser beam causing the two or more dyes each to fluoresce thereby producing a first output signal and a second output signal respectively; and detecting the first output signal and the second output signal. A second of the particles within the capillary being excited using the multiphoton excitation laser beam causing the two or more dyes each to fluoresce thereby producing a third output signal and a forth output signal respectively. The method finally includes comparing a ratio of the first output signal and the second output signal to a ratio of the third output signal and the forth output signal to detect a desired change in the particles.

18 Claims, 8 Drawing Sheets

| Sample No. | G5-FI-FA (nM) | G5-DR-FA (nM) | G5-FI (nM) | G5-DR (nM) | Mean Channel Fluorescence | |
|---|---|---|---|---|---|---|
| | | | | | FITC (a.u.) | Deep Red (a.u.) |
| 1 | 200 | 0 | 0 | 0 | 958 | 5.3 |
| 2 | 180 | 20 | 0 | 0 | 778 | 325.2 |
| 3 | 150 | 50 | 0 | 0 | 608 | 837.8 |
| 4 | 120 | 80 | 0 | 0 | 447 | 1130.3 |
| 5 | 80 | 120 | 0 | 0 | 427 | 2318.3 |
| 6 | 50 | 150 | 0 | 0 | 204 | 2141.3 |
| 7 | 20 | 180 | 0 | 0 | 97 | 2372.3 |
| 8 | 0 | 200 | 0 | 0 | 3.3 | 2365.8 |
| 9 | 0 | 0 | 0 | 0 | 2.86 | 5.86 |
| 10 | 0 | 0 | 200 | 0 | 3.4 | 5.1 |
| 11 | 0 | 0 | 0 | 200 | 2.9 | 12.2 |

QUANTITATIVE TWO-PHOTON FLOW CYTOMETRY

CROSS-REFERENCE TO RELATED APPLICATIONS

This application claims the benefit of U.S. Provisional Application No. 60/611,261, filed on Sep. 17, 2004. The disclosure of the above application is incorporated herein by reference.

GOVERNMENT RIGHTS

This invention was made with government support under Contract No. NAS2-02069 awarded by the National Aeronautics and Space Administration. The Government has certain rights in the invention.

FIELD OF THE INVENTION

The present invention relates to flow cytometry and, more particularly, to a flow cytometer utilizing two-photon excitation in a non-uniform flow system.

BACKGROUND AND SUMMARY OF THE INVENTION

Conventional flow cytometry generally uses single-photon excitation of fluorescence from cells or other particles. By labeling cells with multiple dyes, and by using size measurements via the elastically scattered excitation light, multiple-parameter measurements can be made. The tremendous power of this technique has made it the standard way to quantitate fluorescence in cells. For multiple-dye, multi-wavelength analysis, multiple excitation sources (i.e. lasers) may be required. In light of this arrangement, the layout of such devices can be complex. The complexity of standard flow cytometry also arises from the strict requirements on the fluid flow system, which is designed to guarantee that a single cell is excited at a time. This is typically accomplished using sheath flow by hydrodynamic focusing to produce a linear stream of isolated cells, in conjunction with an elliptically focused excitation laser spot to ensure each cell is excited at the same rate.

The strict requirements and complexity of conventional flow cytometers put limits on their applications, despite of the fact that they are indispensable tools in biological studies. According to the present invention, a novel multiphoton flow cytometer is provided that has a single laser source for excitation of multiple dyes and does not require sheath flow conditions. Thus, the multiphoton flow cytometer not only has a simple configuration, but also opens up a wide range of new applications, such as virus detection and in vivo measurements.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENT

The following description of the preferred embodiment is merely exemplary in nature and is in no way intended to limit the invention, its application, or uses.

Figure 1:
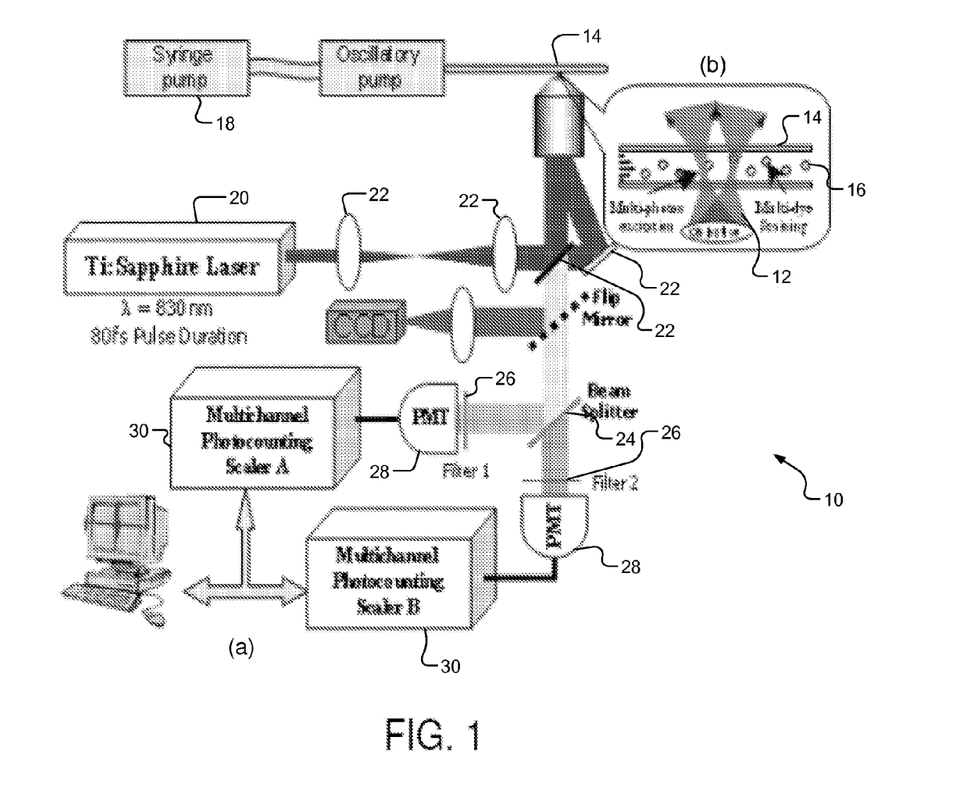
FIG. 1 is a schematic diagram of two-beam, two-channel, two-photon flow cytomety ($T^3FC$) according to the principles of the present invention.

In contrast to conventional flow cytometer, the present invention provides a two-photon excitation using a femtosecond near-infrared (NIR) laser that enables multi-dye analysis to be performed very simply, with greatly relaxed requirements on fluid flow. As illustrated in FIGS. 1(a)-(b), a schematic representation of a two-photon flow cytometry system 10 according to the principles of the present invention is provided. A train of 50-fs pulses at 76-MHz repetition rate (typically with 10 mW average power), generally indicated at 12, is focused into a glass capillary tube 14 (typically 100 µm I.D.). A suspension of the cells to be measured, generally indicated at 16, is held in a syringe pump 18, which forces the suspension through capillary tube 14 at an approximately constant flow rate (typically 5 µL/minute). However, the distribution of cells 16 or other particles are distributed within capillary tube 14 in a non-uniform manner, thus denoting a non-uniform flow. A laser 20, outputting the train of 50-fs pulses, excites fluorescent tags (i.e. dyes) in cells 16 via two-photon transitions. It should be appreciated that cells 16 may include any particles, such as bacteria, stem cells, cancer cells, cells, or any particle have a size of about 3 nanometer or larger.

The nonlinear excitation defines a localized excitation volume or region, which is determined by the focusing optics 22 to be equal or smaller than the size of a single cell. This guarantees that only one cell can be photo-excited at a time. The fluorescence is collected back through at least some of the same optics 22 used for excitation, separated from the excitation beam using a dichroic mirror 24, spectrally filtered using filters 26, and detected using photon-counting photo-multiplier tubes 28. The time-dependent fluorescence signal is measured using a scaler 30; the temporal bin width can be set to correspond to the transit time of a cell through the excitation volume, or it may be set to a much shorter time to enable cell size measurements to be made. Multiple dichroic mirrors and filters are used for multi-wavelength analysis, as illustrated.

In addition to facilitating single-cell excitation, multi-photon excitation has advantages over single-photon excitation as it enables a high signal to background ratio to be easily obtained since the nonspecific background, such as auto-fluorescence and scattering, is much lower. Due to the large separation between the near-infrared (NIR) excitation wavelength and the visible fluorescence emission wavelength, it is easier to attenuate scattered excitation light while collecting the entire spectrum of the fluorescence signal with high efficiency.

In a non-uniform flow, cells 16 at different positions in capillary tube 14 flow with different velocities and, thus, cells 16 flow through the excitation region in random positions. In other words, the localized excitation volume or region represents the space within which cell 16 will be excited and, thus, fluoresce. In conventional cytometry, the cells are carefully aligned and pass directly through any excitation region. Thus, if no change occurs in the cell, the conventional system outputs a consistent flourescence. However, in non-uniform flow (i.e. in vivo or any case where cells 16 are not carefully aligned for excitation), the varying position of cells 16 relative to the localized excitation region will result in varying flourescence, irrespective of any change in cell 16. As will be discussed herein, the present invention is capable of analyzing cells 16 in this non-uniform flow irrespective of the relative positioning of cell 16 to localized excitation region.

Figure 2:
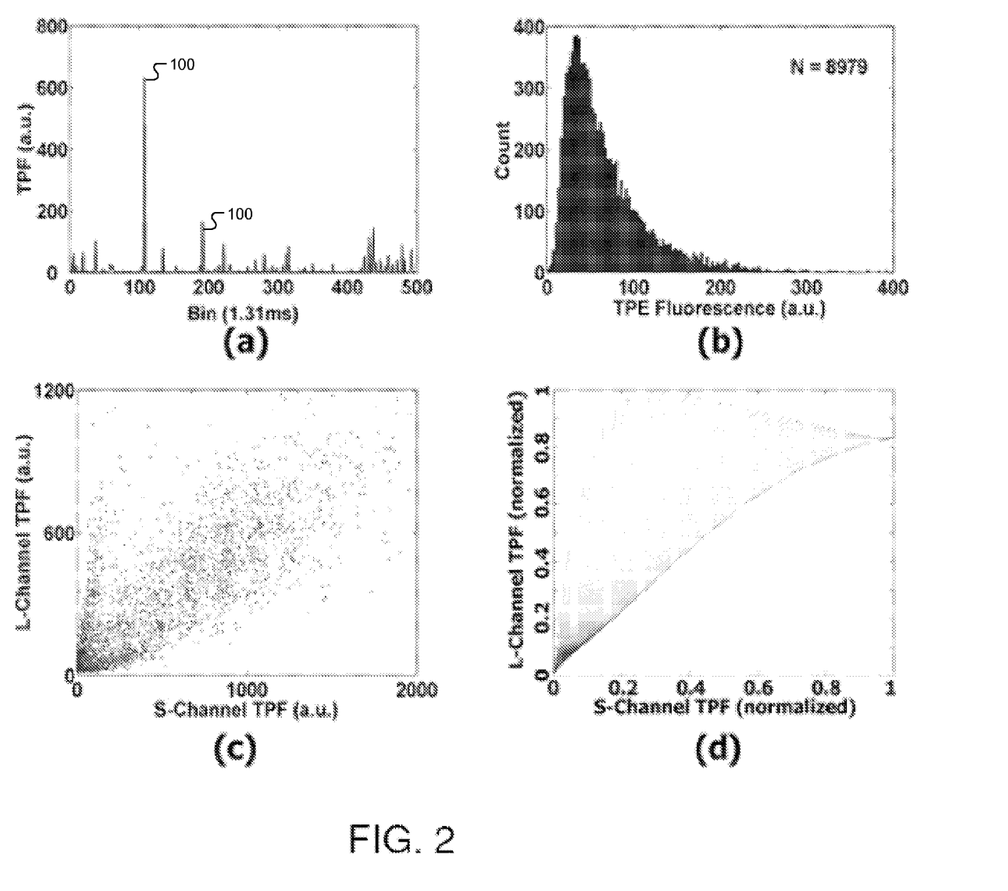
FIG. 2(a) is a graph illustrating single channel raw data wherein each peak represents a labeled cell passing through the laser focus.
FIG. 2(b) is a histogram of the intensity distribution of peaks in a single channel.
FIG. 2(c) is a two-channel dot plot of mouse peripheral mononuclear blood cells (PMBC) stained with CFSE and DeepRed.
FIG. 2(d) is a simulated two-channel dot plot of dual dye stained 10 um microspheres.
Figure 3:
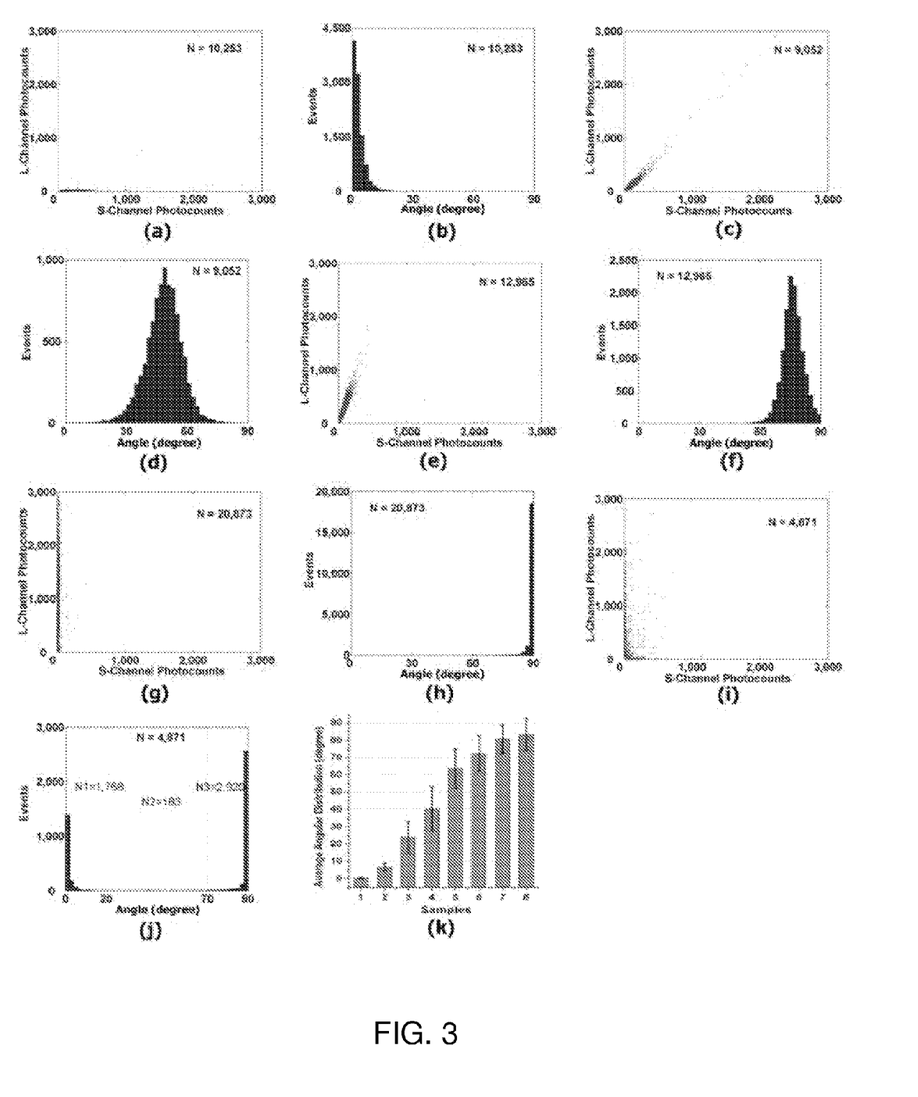
FIGS. 3(a)-(j) are corresponding graphs illustrating two-channel dot plot and angular distribution of KB cell samples stained with G5-FI-FA and G5-DR-FA at different concentrations, such that (a) and (b) are two-channel dot plot and angular distribution histogram from sample 1, (c) and (d) are from sample 2, (e) and (f) are from sample 3, (g) and (h) are from sample 8, (i) and (j) are from a mixture of sample 1 and sample 8 at volume ratio of 1:1.
FIG. 3(k) illustrates the average angular distribution of cell samples from 1 to 11.

Referring now to FIG. 2(a), a two-photon excited fluorescence signal versus time (bin number) from cells stained with a single dye is illustrated. Each peak 100 (only some numbers in the figure) represents a labeled cell passing through the laser focus. In conventional flow cytometry, the distribution of the fluorescence intensity of labeled cells usually peaks at a certain value depending on the uptake of the probe used, so that fluorescence gating can be used to differentiate different cell populations for single-parameter analysis. However, due to non-uniform excitation, the intensity distribution of the peaks (FIG. 2(b)) spreads out from just above background to its maximum possible signal level (corresponding to cells which have the highest fluorophore concentration and which flow directly through the center of the excitation spot). Thus, the fluorescence signal level alone cannot be used as a parameter to differentiate cell populations. For any quantitative measurement of the fluorescence signal indicating biological properties, it is necessary to measure the fluorescence signal level together with spectral information related to biological changes. The present invention creates at least two fluorescence-collecting channels at different wavelengths, which separate optical signals into long and short wavelengths, so that any spectral change is reflected in the ratios of fluorescence signals in these channels. This ratiometric measurement may either rely on a spectral shift induced in a single dye, or a cell may be labeled with two dyes ("trigger" and "reporter" dyes).

In order to investigate the conditions which would enable signal quantification using trigger and reporter dyes, mouse peripheral mononuclear blood cells (PMBC) were stained with two dyes: carboxyfluorescein succinimidyl ester (CFSE) and DeepRed. The CFSE fluorochrome is a biocompatible dye that does not affect viability of stained cells for a prolonged period of time, and is used to indicate which cells have been labeled, the "trigger". DeepRed is a cell-permeating probe that binds to the outer membrane of mitochondria in living cells and is an indicator of cell viability, thus it serves as the "reporter". The ratio of reporter over trigger fluorescence signal should indicate the viability of a single cell. The fluorescence was filtered such that the short wavelength detection channel (S-channel) only receives a fluorescence signal from the CFSE, while the long wavelength detection channel (L-channel) only receives a fluorescence signal from the DeepRed.

For dual dye stained normal PMBC, a wide distribution was observed in a two-channel dot plot of the signal versus reporter fluorescence amplitudes (FIG. 2(c)). In order to make ratiometric measurements, it is essential that the fluorescence amplitudes of signal and reporter be correlated. The wide distribution observed indicates the signals are not correlated and hence it would be difficult to distinguish viable from non-viable cells. One reason for the lack of correlation could be that there is no correlation between the concentrations of the two dyes within the cells, although saturation of the dye uptake should yield a correlation, which was not observed. A second reason can be different spatial distributions of the two dyes within each cell: confocal microscopy images show that CFSE is uniformly distributed within the whole volume of the cells, while DeepRed stains only at the cell membrane. Using a uniformly distributed fluorescent sphere (10 µm) as a model for the CFSE distribution and a fluorescent shell (10 µm) as the model for DeepRed, a computer simulation incorporating an accurate model of the two-photon excitation volume shows that the two channels become uncorrelated (FIG. 2(d)).

Figure 8:
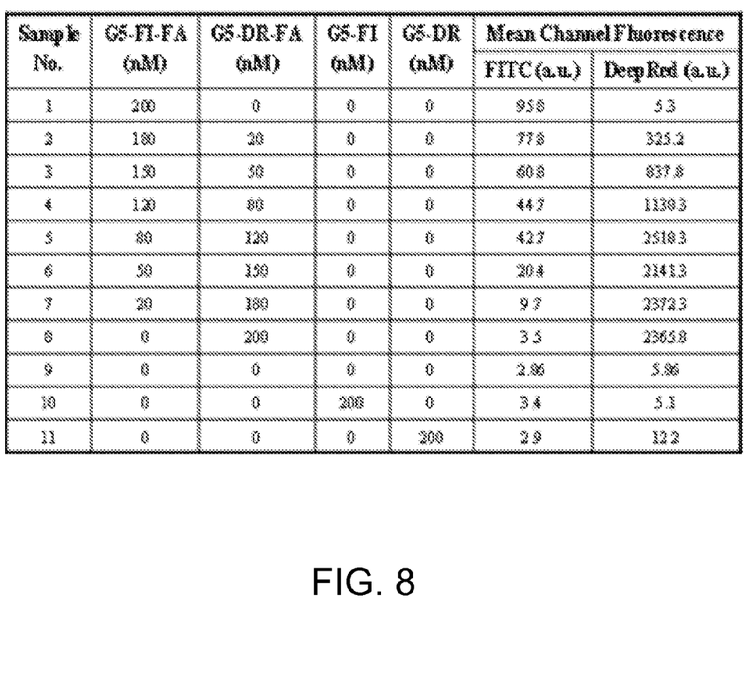
FIG. 8 lists the concentration of dye conjugates used to incubate KB cell samples and their mean channel fluorescence from conventional single photon flow cytometer.

One solution to establish the required correlation between the trigger and reporter dyes is to use targeted fluorochromes. For example, two dyes could be conjugated onto a nanoparticle which is taken up into the cells via specific receptors. The approach of the present invention is simple: the dye molecules are linked separately onto nanoparticles which have the same targeting agent. By competing for the same receptors, the dye concentrations in the cell become correlated. Specifically, for proof of concept the KB cell model was selected, which is an epidermoid carcinoma cell line known to express the receptor for folic acid (FA). The nanoparticles used to carry the FA targeting agent and fluorescent molecule are PAMAM dendrimers 10. Previously, studies have shown that the KB cells bind and internalize FA-conjugated dendrimers in a receptor-mediated fashion. KB cells were treated with the dendrimer-FITC-folic acid conjugate (G5-Fl-FA) and dendrimer-DeepRed-folic acid conjugate (G5-DR-FA) at different concentrations (FIG. 8), which contain FITC (Fl) and Deep Red (DR) as the respective fluorescent detecting agents. As the dendrimer-dye-folic acid conjugate concentration varies, the fluorescence signals from the KB cell samples (sample 1 to 8) are in well separated clusters in a two-parameter (S-channel vs. L-channel) dot plot (see FIGS. 3(a), (c), (e), and (g)). In addition, the angular distribution of the ratio of these samples peaks at different values (FIGS. 3(b), (d), (f), and (h)). When flowing the mixture of KB cell samples of different incubation condition (1 and 8) through the capillary system of the present invention, signals from different samples stay in their corresponding cluster (FIG. 3(i)), as well as their angular distributions (FIG. 3(j)). The average angular distribution of these samples (1 to 8) increases as the concentration ratio of G5-Fl-FA to G5-DR-FA decreases (FIG. 3(k)). For unstained KB cell sample (sample 9) or KB cell samples stained with dendrimer-dye conjugates (sample 10 and 11), the number of cells detected is three orders of magnitude lower compared with KB cell samples stained with dendrimer-dye-folic acid conjugates and their angular distribution is random (FIG. 3(k)). This shows that folic acid in the dendrimer conjugate functions as the specific cell targeting agent. Linear fit of the average angular distribution to incubation dye concentration confirms the uptake of the dendrimer-dye-folic acid conjugates is proportional to the conjugate concentration during cell incubation. Due to the difference of fluorescence quantum yield and two-photon excitation cross section between FITC and DeepRed, the number of photons detected in the L-channel is roughly ten times of the number detected in the S-channel.

Monitoring Circulating Fluorescent Microspheres and Fluorescence-Labeled Cells In Vivo To demonstrate the ability to perform multicolor detection of circulating fluorescent particles in vivo, fluorescent microspheres or fluorescence-labeled cells were injected through the tail vein of a mouse. Two-photon flow cytometry measurements were performed at a blood vessel in the mouse ear. Before the injection of the fluorescent microspheres or the DeepRed-labeled splenocytes, the background signals in both S-channel and L-channel were recorded with the femtosecond NIR laser beam focused in various locations within the mouse ear. The measured background control traces before each injection are shown to the left of the line 200 in FIGS. 5(a) and (d). The thresholds were adjusted so that no peaks exist in the control traces. Line 200 and line 202 correspond to the first and second injections, respectively. Lines 204 and 206 (FIG. 5(d)) correspond to 2 hours after first injection and 1 day after first injection, respectively.

Figure 5:
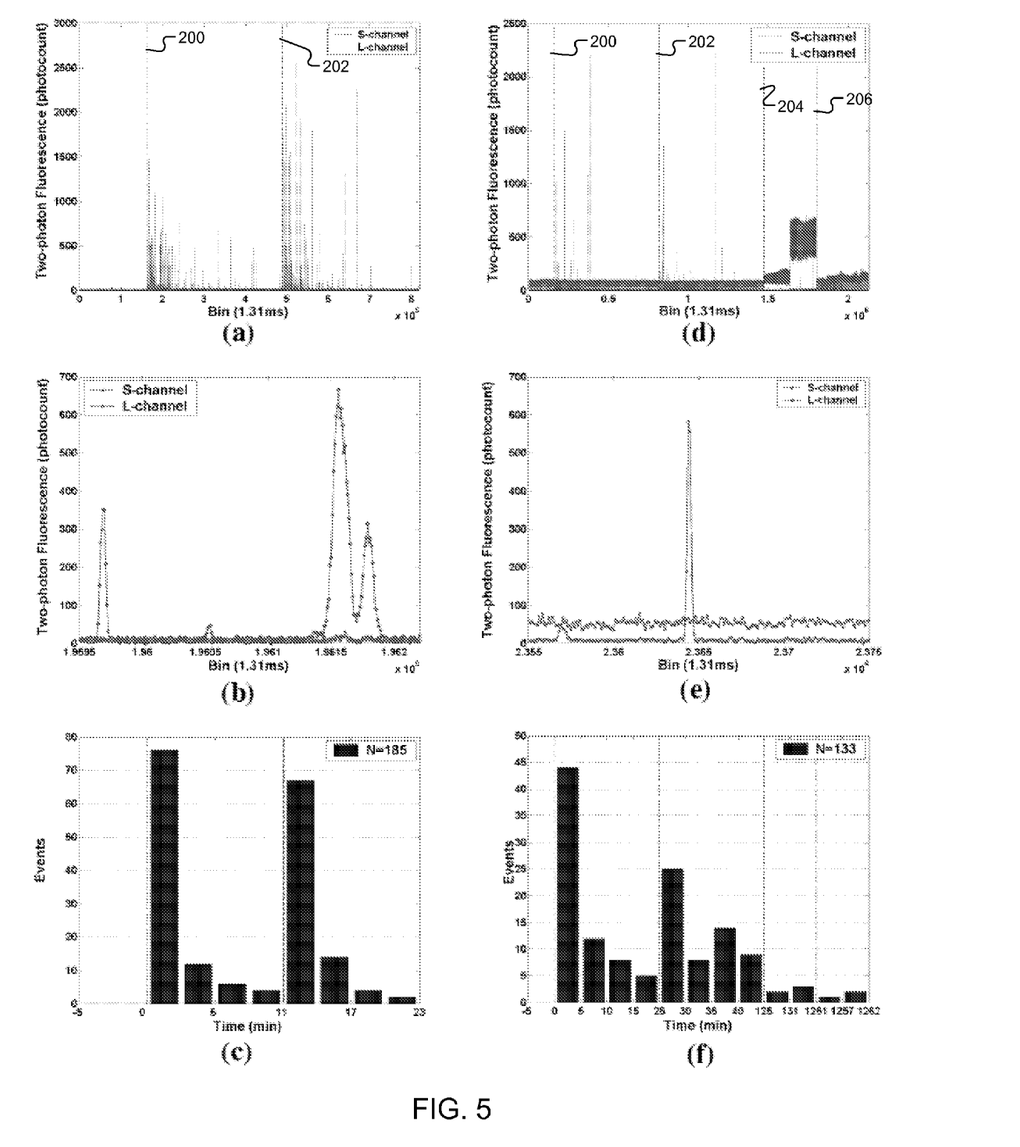
FIG. 5(a) illustrates S-channel and L-channel traces from an ear blood vessel of a CD-1 mouse injected with 2.3×109 yellow-green fluorescent (Ex505/Em515) 2.0 µm microspheres at time zero and 11 minutes after, wherein the control traces are shown to the left of the orange dashed line and each spike in the S-channel corresponds to the fluorescent burst from microspheres passing through the excitation region.
FIG. 5(b) illustrates an enlarged view of the dual-channel raw data showing detail of individual fluorescent peaks of FIG. 5(a)
FIG. 5(c) illustrates a number of detected events at different time points before and after injection, wherein each time point is represented by number of peaks above the background threshold during a period of 107 seconds.
FIG. 5(d) illustrates S-channel and L-channel traces from an ear blood vessel of a NU/NU CD-1 mouse injected with 3.6×106 DeepRed-labeled splenocytes at time zero and 25 minutes after, wherein each spike in the L-channel corresponds to the fluorescent burst from DeepRed-labeled splenocytes passing through the excitation region.
FIG. 5(e) illustrates an enlarged view of the dual-channel raw data of FIG. 5(d)
FIG. 5(f) illustrates a number of detected events at different time points before and after injection, wherein each time point is represented by the number of peaks above the background threshold during a period of 214 seconds.

The background in the S-channel of the mouse injected with DeepRed-labeled cells (FIG. 5(e)) was higher than that injected with fluorescence microspheres (FIG. 5(b)). This is because a different type of mouse was used and the laser was focused to a different site in the mouse ear for the two experiments. In addition, the S-channel background in FIG. 5(d) changed dramatically for the data taken two hours and one day after the initial injection. This can be attributed to the tremble of the anesthetized mouse during data acquisition. In spite of this, the background fluorescence in the L-channel remains at a low level throughout the whole experiments, allowing fluorescent peaks to be selected.

FIG. 5(a) illustrates the S-channel and L-channel traces of a mouse injected with the 2.0 µm yellow-green fluorescent microspheres, in which a peak in the S-channel corresponds to a microsphere passing through the excitation region (FIG. 5(b)). FIG. 5(d) shows the two-channel traces of a mouse injected with DeepRed-labeled splenocytes, in which a peak in the L-channel corresponds to a cell (FIG. 5(e)). Thus, circulating 2.0 µm yellow-green fluorescent microspheres and DeepRed-labeled splenocytes were detected in short and long spectral detection channels, respectively. The two-channel detection method permits differentiation of different cell or particles based on the fluorescence wavelength. It is also possible to conduct two-channel ratiometric measurements in vivo as demonstrated previously in vitro.

The double-peak event in FIG. 5(b) is probably the fluorescent trace of clogged fluorescent microspheres. For the fluorescent microspheres, about 20% of the detected events contained double peaks. For DeepRed-labeled splenocytes, almost no large peaks were observed. A double-peak event is treated as a single event if the fluorescent signal between the two peaks does not fall below the background threshold value.

The number of detected fluorescent microspheres and DeepRed-labeled splenocytes at different time points is shown in FIGS. 5(c) and (f), respectively. For both of experiments, fluorescent microspheres or DeepRed-labeled cells were detected in the ear blood vessel immediately after tail vein injection (less than 30 seconds delay), which was indicated by the sudden increases in frequency of events. The frequency dropped to less than 10% within the first 10 to 20 minutes. The frequency went up again with reinjection of the same amount of fluorescent microspheres or DeepRed-labeled splenocytes. Similar depletion dynamics was observed. The experiments were repeated at the same location in the mouse ear 2 hours and 1 day after the initial injection. No fluorescent microspheres were observed (not show here), while a few circulating DeepRed-labeled splenocytes were detected.

Figure 6:
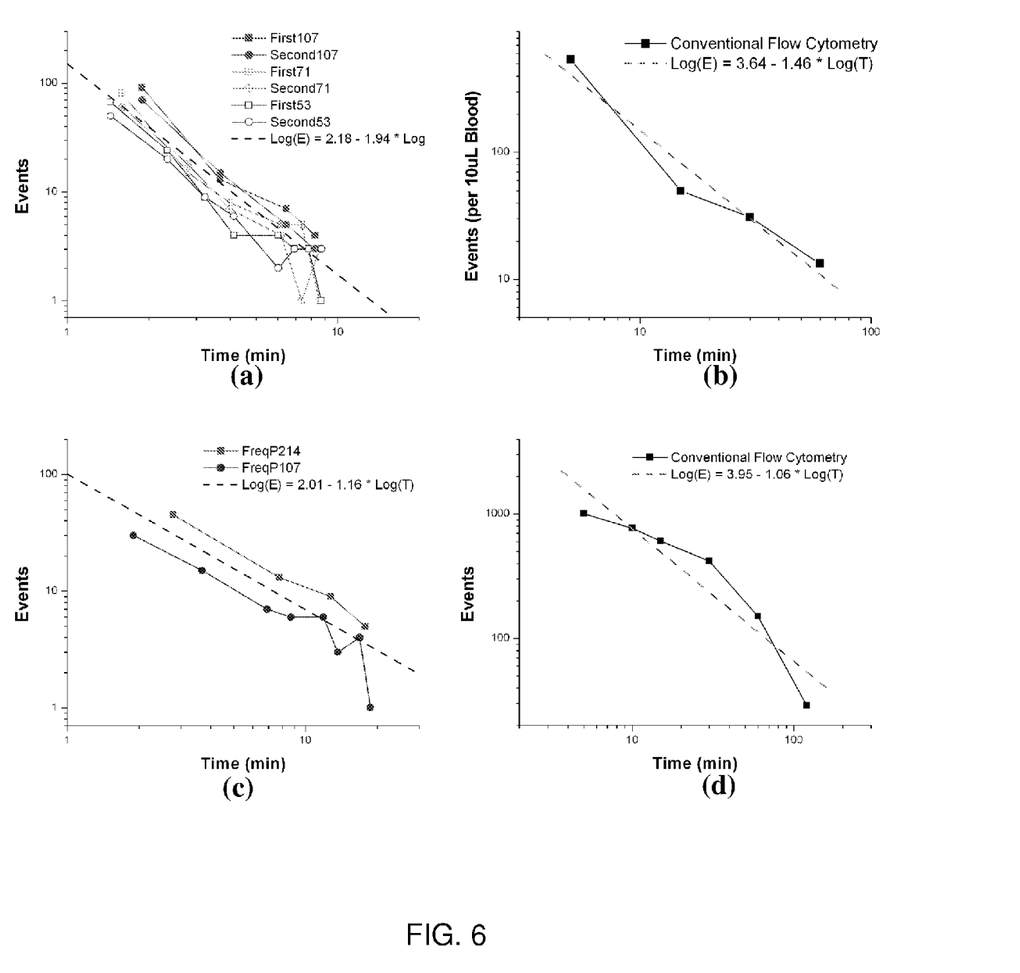
FIG. 6(a) illustrates 10-minute frequency dynamics in the blood vessel of a CD-1 mouse after the first (square marker) and the second (round marker) injection of 2.3×109 yellow-green fluorescent 2.0 µm microspheres.
FIG. 6(b) illustrates frequency dynamics obtained by ex vivo analysis using a conventional flow cytometer, wherein blood was drawn at different time points from the mouse after injection of the same dose of microsphere solution.
FIG. 6(c) illustrates 20-minute frequency dynamics in the blood vessel of a NU/NU CD-1 mouse after the first injection of 3.6×106 DeepRed-labeled splenocytes.
FIG. 6(d) illustrates frequency dynamics obtained by ex vivo analysis using a conventional flow cytometer, wherein blood was drawn at different time points from the mouse after injection of the same dose of DeepRed-labeled splenocytes.

The depletion dynamics of circulating fluorescent microspheres in CD-1 mice and DeepRed-labeled splenocytes in NU/NU CD-1 mice using the in vivo two-photon flow cytometer and conventional flow cytometer is shown in FIG. 6. For the CD-1 mouse injected with fluorescent microspheres, the S-channel traces after the first and second injection were used to calculate the frequency of detected events (FIG. 6(a)). For the NU/NU CD-1 mouse injected with DeepRed-labeled splenocytes, the L-channel trace after the first injection was used (FIG. 6(c)). The frequency was calculated as the number of events within a certain time period. The time points beyond 10 or 20 minutes were not used to generate the fitting, as the number of detected cells fell below 1 event per minute. The number of fluorescent microspheres (FIG. 6(b)) or CFSE-labeled splenocytes (FIG. 6(d)) in 10 uL of blood drawn at different time points after injection was detected ex vivo using a conventional flow cytometer.

The in vivo flow cytometry results show that the fluorescent microspheres deplete faster in the circulation of a CD-1 mouse than fluorescence-labeled splenocytes in NU/NU CD-1 mouse. The average slope coefficients are −1.94 and −1.16 for circulating fluorescent microspheres and DeepRed-labeled splenocytes, respectively. This difference in depletion rate was also observed from the ex vivo flow cytometry results, where the slope coefficients are −1.46 and −1.06 for circulating fluorescent microspheres and CFSE-labeled splenocytes, respectively. The reasons for the frequency drop could be that the microbeads or splenocytes clogged in the blood stream, stuck to the blood vessel surfaces, were removed by lysis or phagocytosis, or were filtered by organs in the circulation. The different depletion rates indicate the circulation time of splenocytes in an immmunodeficient NU/NU CD-1 mouse is longer than that of fluorescent microspheres in a CD-1 mouse.

For both circulating fluorescent microspheres and fluorescence-labeled splenocytes, the depletion rate in the first 10 minutes after injection obtained by in vivo flow cytometry is larger than the rate in the first 1.5 hours obtained by ex vivo flow cytometry analysis. The difference of the depletion rates from in vivo and ex vivo measurements could be attributed to the different time scales in the depletion process. It could also be the systematic error in the ex vivo method introduced by the significant delay between blood withdrawal and flow cytometry analysis.

Monitoring Fluorescent Dye Staining Process In Vivo

Figure 7:
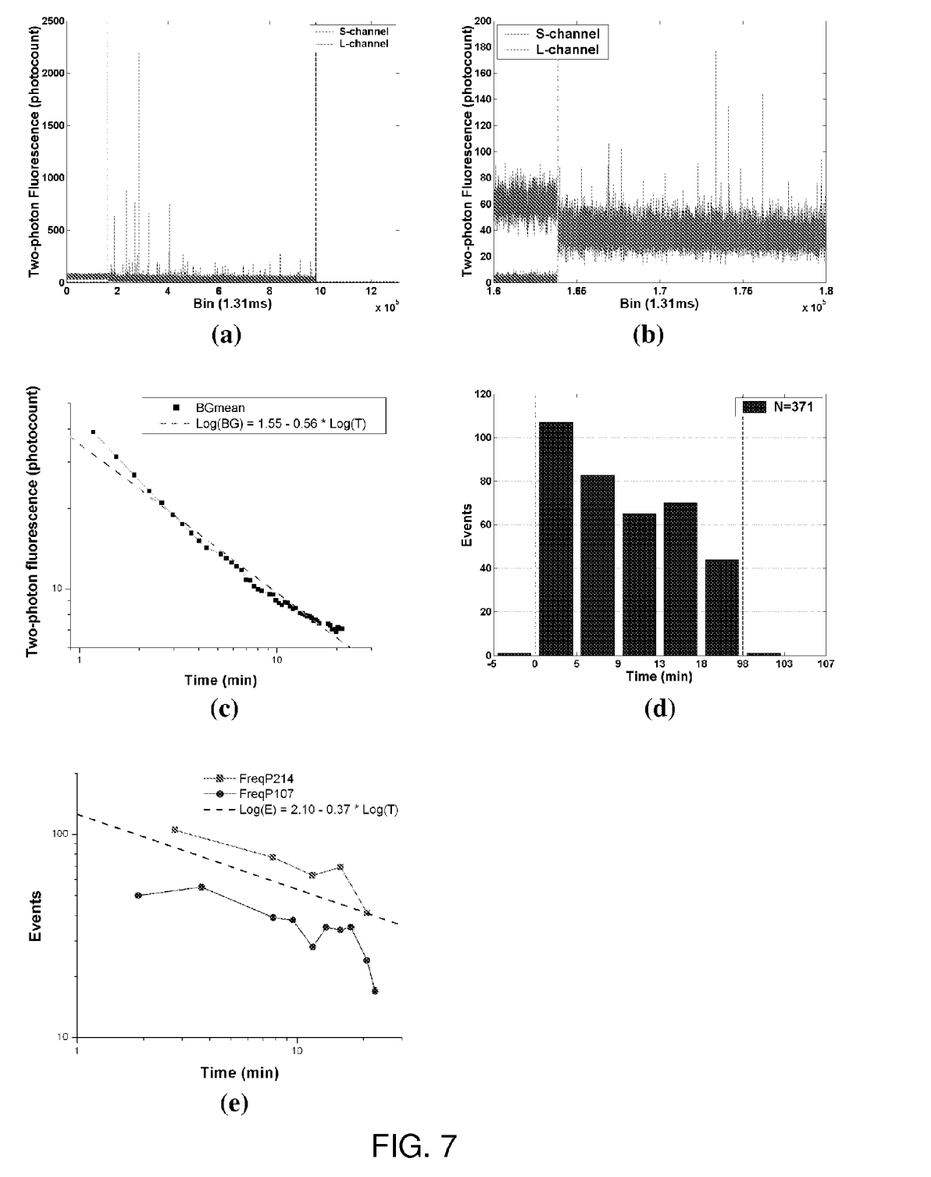
FIG. 7(a) illustrates S-channel and L-channel traces from a blood vessel in the ear of a NU/NU CD-1 mouse injected with 300 µL (5 µM) DeepRed solution at time zero, wherein each spike in the L-channel corresponds to the fluorescent burst from DeepRed fluorophores in cells passing through the excitation region.
FIG. 7(b) illustrates an enlarged dual-channel raw data at the time of injection showing the background rise in the L-channel after injection of free DeepRed dye solution.
FIG. 7(c) illustrates the background two-photon excited fluorescent signal in the L-channel at different time points after the injection of DeepRed dye solution.
FIG. 7(d) illustrates a number of detected events at different time points before and after injection.
FIG. 7(e) illustrates 20-minute peak frequency dynamics in the blood vessel of a NU/NU CD-1 mouse after the injection of 300 µL of DeepRed solution.

The two-channel fluorescence traces from an ear blood vessel were monitored as free DeepRed dye solution was injected through the tail vein (FIG. 7(a)). As shown in FIG. 7(b), the background signal in the long channel rose immediately after the injection, due to the presence of the DeepRed fluorophores in the mouse blood. After the injection, the background signal gradually decreased, as the dye molecules permeated through the blood vessel walls or were filtered out of the circulation. The average background signal at different time points is plotted against time in a log scale (FIG. 7(c)), and a linear fit of the signal decay reveals a slope coefficient of −0.56. Compared with the depletion rate of fluorescent microspheres or fluorescence-labeled splenocytes, the background decay rate is much slower.

The peaks above the background were also observed in the L-channel trace signal. DeepRed is a cell-permeating probe that binds to the outer membrane of mitochondria in living cells and measures their viability. As the DeepRed dye solution circulates in the vasculature, it labels the circulating lymphocytes. Therefore, the peaks should correspond to the in vivo labeled cells passing through the two-photon excitation region. The number of peaks above threshold at different time points was acquired (FIG. 7(d)). The threshold was adjusted according to the gradually changing background fluorescence signal. The frequency of in vivo labeled cells decreases after the injection. An average depletion rate of −0.37 was obtained by fitting the number of detected events in the first 20 minutes after injection (FIG. 7(e)). This rate is much slower than those of fluorescent microspheres or fluorescence-labeled splenocytes shown previously. One and half hours after the initial injection of free DeepRed dye, only one event was observed in a 6-minute interval.

Figure 4:
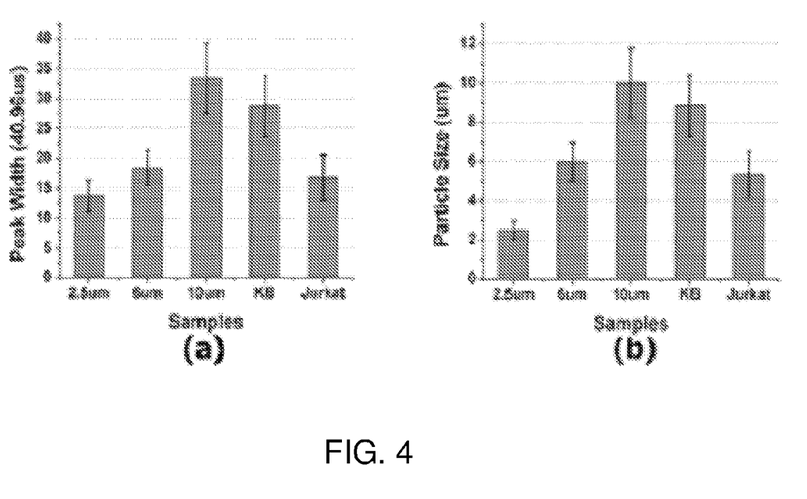
FIGS. 4(a)-(b) illustrate size measurements made using $T^3FC$ of the present invention, such that (a) represents the average peak width (normalized duration time of cell passing through one excitation volume) of different samples, wherein 2.5 um, 6 um, and 10 um are the diameter of fluorescent microspheres, and (b) represents the actual particle size of the samples after deconvolution algorisms.

With appropriate trigger and reporter dye labeling, two-photon flow cytometry becomes possible in greatly simplified flow systems. This opens the way to quantitative cytometry in simple and compact microfluidics systems, or in vivo. Quantitative size measurements can also be done in the present system even under conditions of non-uniform flow. This is done in conventional cytometry via elastic light scattering. In the present invention, the excitation beam is split into two separate foci aligned along the capillary flow direction; the spot size is set to be smaller than the cell size. The velocity of each cell is measured via the time delay between the two excitation spots, and then the size is determined via the time it takes to pass through one of the focal spots. Size measurements made this way are shown in FIG. 4 for calibrated microspheres of various sizes as well as several different types of cells.

Viral and similar submicroscopic particles are well outside the light scattering detection range of conventional flow cytometers. The (ungated) light scattering detection limit of commercial instruments is typically around 300-500 nm as obtained with polymer particles and considerably larger for cells such as bacteria and algae due to their high water content and correspondingly lower refractive index. The other limit comes from the debris in the sheath water used in conventional flow cytometer. In the $T^3FC$, the detection background is eliminated because the sheath flow is not used here—the ratiometric fluorescence measurements are used to quantify the particles in the small detection volume. Thus, the $T^3FC$ overcomes the detection size limitation of a conventional flow cytometer. $T^3FC$, therefore, can be used to detect nanometer size particles such as viruses. This feature significantly increases the applications of current flow cytometers.

The description of the invention is merely exemplary in nature and, thus, variations that do not depart from the gist of the invention are intended to be within the scope of the invention. Such variations are not to be regarded as a departure from the spirit and scope of the invention.

TABLE 1

| Sample No. | G5-FI-FA (nM) | G5-DR-FA (nM) | G5-FI (nM) | G5-DR (nM) | Mean Channel Fluorescence | |
|---|---|---|---|---|---|---|
| | | | | | FITC (a.u.) | Deep Red (a.u.) |
| 1 | 200 | 0 | 0 | 0 | 958 | 53 |
| 2 | 180 | 20 | 0 | 0 | 778 | 325.2 |
| 3 | 150 | 50 | 0 | 0 | 608 | 837.8 |
| 4 | 120 | 80 | 0 | 0 | 447 | 1138.3 |
| 5 | 80 | 120 | 0 | 0 | 427 | 2518.3 |
| 6 | 50 | 150 | 0 | 0 | 204 | 2141.3 |
| 7 | 20 | 180 | 0 | 0 | 97 | 2372.3 |
| 8 | 0 | 200 | 0 | 0 | 35 | 2365.8 |
| 9 | 0 | 0 | 0 | 0 | 2.85 | 5.86 |
| 10 | 0 | 0 | 200 | 0 | 34 | 5.1 |
| 11 | 0 | 0 | 0 | 200 | 29 | 12.2 |

What is claimed is:

1. A method of multi-dye analysis of particles using flow cytometer, said method comprising:
labeling particles to be detected using two or more dyes, said two or more dyes comprising a trigger dye and a reporter dye, said trigger dye is selected from carboxyfluorescein succinimidyl ester (CFSE) and fluorescein isothiocyanate (FITC), said reporter dye is DeepRed;
suspending said particles within a non-uniform flow in a capillary;
exciting a first of said particles within said capillary using a multiphoton excitation laser beam causing said two or more dyes each to fluoresce thereby producing a first output signal and a second output signal respectively;
detecting said first output signal and said second output signal;
exciting a second of said particles within said capillary using said multiphoton excitation laser beam causing said two or more dyes each to fluoresce thereby producing a third output signal and a fourth output signal respectively; and
comparing a ratio of said first output signal and said second output signal to a ratio of said third output signal and said fourth output signal to detect a desired change in said particles.

2. The method according to claim 1 wherein said first output signal has a first wavelength and said second output signal has a second wavelength.

3. The method according to claim 1 wherein said suspending said particles within said non-uniform flow in said capillary comprises creating said non-uniform flow using a pump.

4. The method according to claim 1 wherein said suspending said particles within said non-uniform flow in said capillary comprises suspending said particles within a non-uniform, pulsatile flow.

5. The method according to claim 1 wherein said suspending said particles within said non-uniform flow in said capillary comprises suspending bacteria within said non-uniform flow.

6. The method according to claim 1 wherein said suspending said particles within said non-uniform flow in said capillary comprises suspending cancer cells within said non-uniform flow.

7. The method according to claim 1 wherein said suspending said particles within said non-uniform flow in said capillary comprises suspending stem cells within said non-uniform flow.

8. The method according to claim 1 wherein said suspending said particles within said non-uniform flow in said capillary comprises suspending a virus within said non-uniform flow.

9. The method according to claim 1 wherein said suspending said particles within said non-uniform flow in said capillary comprises suspending a particle having a diameter of about 1 nanometers within said non-uniform flow.

10. The method according to claim 1 wherein said suspending said particles within said non-uniform flow is performed in vivo.

11. A method of multi-dye analysis of particles using flow cytometer, said method comprising:
labeling particles to be detected using two or more dyes, a first of said two or more dyes being selected from carboxyfluorescein succinimidyl ester (CFSE) and fluorescein isothiocyanate (FITC), a second of said two or more dyes is DeepRed;
pumping said particles through a capillary;
exposing a first of said particles within said capillary using a multiphoton excitation laser beam causing said two or more dyes to fluoresce at a first wavelength and at a second wavelength, said first wavelength being different from said second wavelength;
detecting said first wavelength and said second wavelength of said fluorescence;
exposing a second of said particles within said capillary using said multiphoton excitation laser beam causing said two or more dyes to fluoresce at a third wavelength and at a fourth wavelength, said third wavelength being different from said fourth wavelength;
detecting said third wavelength and said fourth wavelength of said fluorescence; and
comparing a ratio of said first wavelength and said second wavelength to a ratio of said third wavelength and said fourth wavelength to detect a change therebetween.

12. The method according to claim 11 wherein said pumping said particles through said capillary comprises pumping said particles through said capillary in a non-uniform flow.

13. The method according to claim 11 wherein said pumping said particles through said capillary comprises pumping a particle chosen from the group consisting essentially of bacteria, virus, cancer cell, and stem cell through said capillary.

14. The method according to claim 11 wherein said pumping said particles through said capillary comprises pumping a particle having a diameter of about 1 nanometers through said capillary.

15. The method according to claim 11 wherein said pumping said particles through said capillary is performed in vivo.

16. A method of multi-dye analysis of particle using flow cytometer, said method comprising:
labeling a particle to be detected using two or more dyes, said two or more dyes comprising a trigger dye and a reporter dye, said trigger dye is selected from carboxyfluorescein succinimidyl ester (CFSE) and fluorescein isothiocyanate (FITC), said reporter dye is DeepRed;

suspending said particle through a capillary without sheath flow;

exciting said particle within said capillary using a multiphoton excitation laser beam causing said two or more dyes to fluoresce thereby producing at least a first output signal and a second output signal;

detecting said output signals; and determining presence of said particle in response to said output signals.

17. The method according to claim 16 wherein said suspending said particle through said capillary comprises suspending said particle chosen from the group consisting essentially of bacteria, virus, cancer cell, and stem cell through said capillary.

18. The method according to claim 16 wherein said suspending said particles through said capillary is performed in vivo.

* * * * *